(12) United States Patent
Paolini, Jr. et al.

(10) Patent No.: US 12,186,514 B2
(45) Date of Patent: *Jan. 7, 2025

(54) DIGITAL MICROFLUIDIC DELIVERY DEVICE

(71) Applicant: E INK CORPORATION, Billerica, MA (US)

(72) Inventors: Richard J. Paolini, Jr., Framingham, MA (US); Stephen J. Telfer, Arlington, MA (US); Timothy J. O'Malley, Westford, MA (US); Brian D. Bean, Newton, MA (US)

(73) Assignee: E Ink Corporation, Billerica, MA (US)

( * ) Notice: Subject to any disclaimer, the term of this patent is extended or adjusted under 35 U.S.C. 154(b) by 218 days.

This patent is subject to a terminal disclaimer.

(21) Appl. No.: 17/974,212

(22) Filed: Oct. 26, 2022

(65) Prior Publication Data

US 2023/0037658 A1 Feb. 9, 2023

Related U.S. Application Data

(63) Continuation of application No. 16/601,641, filed on Oct. 15, 2019, now Pat. No. 11,511,096.

(60) Provisional application No. 62/745,718, filed on Oct. 15, 2018.

(51) Int. Cl.
*A61M 35/00* (2006.01)

(52) U.S. Cl.
CPC ..... *A61M 35/10* (2019.05); *A61M 2205/0238* (2013.01); *A61M 2205/82* (2013.01)

(58) Field of Classification Search
CPC .......... A61M 35/10; A61M 2205/0238; A61M 2205/82
See application file for complete search history.

(56) References Cited

U.S. PATENT DOCUMENTS

| 4,573,995 A | 3/1986 | Chen et al. |
| 4,708,716 A | 11/1987 | Sibalis |
| 5,080,646 A | 1/1992 | Theeuwes et al. |
| 5,311,337 A | 5/1994 | McCartney, Jr. |

(Continued)

FOREIGN PATENT DOCUMENTS

| CN | 105665043 A | 6/2016 |
| JP | H06186575 A | 7/1994 |

(Continued)

OTHER PUBLICATIONS

Abdelgawad, Mohamed et al., "The Digital Revolution: A New Paradigm for Microfluidics", Advanced Materials, vol. 21, pp. 920-925,(2009).

(Continued)

*Primary Examiner* — Lauren P Farrar
(74) *Attorney, Agent, or Firm* — Rajesh Vallabh (57) ABSTRACT

An active molecule delivery system whereby active molecules can be released on demand and/or a variety of different active molecules can be delivered from the same system and/or different concentrations of active molecules can be delivered from the same system. The invention is well-suited for delivering pharmaceuticals to patients transdermally. In some embodiments, the system includes two separate reservoirs and a mixing area thereby allowing precursors to be mixed immediately before transdermal delivery.

10 Claims, 8 Drawing Sheets

(56) References Cited

U.S. PATENT DOCUMENTS

| | | |
|---|---|---|
| 5,930,026 A | 7/1999 | Jacobson et al. |
| 6,118,426 A | 9/2000 | Albert et al. |
| 6,124,851 A | 9/2000 | Jacobson |
| 6,177,921 B1 | 1/2001 | Comiskey et al. |
| 6,232,950 B1 | 5/2001 | Albert et al. |
| 6,241,921 B1 | 6/2001 | Jacobson et al. |
| 6,252,564 B1 | 6/2001 | Albert et al. |
| 6,312,304 B1 | 11/2001 | Duthaler et al. |
| 6,312,971 B1 | 11/2001 | Amundson et al. |
| 6,376,828 B1 | 4/2002 | Comiskey |
| 6,392,786 B1 | 5/2002 | Albert |
| 6,413,790 B1 | 7/2002 | Duthaler et al. |
| 6,422,687 B1 | 7/2002 | Jacobson |
| 6,445,489 B1 | 9/2002 | Jacobson et al. |
| 6,473,072 B1 | 10/2002 | Comiskey et al. |
| 6,480,182 B2 | 11/2002 | Turner et al. |
| 6,498,114 B1 | 12/2002 | Amundson et al. |
| 6,504,524 B1 | 1/2003 | Gates et al. |
| 6,506,438 B2 | 1/2003 | Duthaler et al. |
| 6,512,354 B2 | 1/2003 | Jacobson et al. |
| 6,518,949 B2 | 2/2003 | Drzaic |
| 6,531,997 B1 | 3/2003 | Gates et al. |
| 6,545,291 B1 | 4/2003 | Amundson et al. |
| 6,639,578 B1 | 10/2003 | Comiskey et al. |
| 6,657,772 B2 | 12/2003 | Loxley |
| 6,664,944 B1 | 12/2003 | Albert et al. |
| D485,294 S | 1/2004 | Albert |
| 6,683,333 B2 | 1/2004 | Kazlas et al. |
| 6,704,133 B2 | 3/2004 | Gates et al. |
| 6,710,540 B1 | 3/2004 | Albert et al. |
| 6,724,519 B1 | 4/2004 | Comiskey et al. |
| 6,753,999 B2 | 6/2004 | Zehner et al. |
| 6,816,147 B2 | 11/2004 | Albert |
| 6,819,471 B2 | 11/2004 | Amundson et al. |
| 6,825,068 B2 | 11/2004 | Denis et al. |
| 6,825,829 B1 | 11/2004 | Albert et al. |
| 6,825,970 B2 | 11/2004 | Goenaga et al. |
| 6,831,769 B2 | 12/2004 | Holman et al. |
| 6,842,279 B2 | 1/2005 | Amundson |
| 6,842,657 B1 | 1/2005 | Drzaic et al. |
| 6,865,010 B2 | 3/2005 | Duthaler et al. |
| 6,873,452 B2 | 3/2005 | Tseng et al. |
| 6,900,851 B2 | 5/2005 | Morrison et al. |
| 6,909,532 B2 | 6/2005 | Chung et al. |
| 6,922,276 B2 | 7/2005 | Zhang et al. |
| 6,950,220 B2 | 9/2005 | Abramson et al. |
| 6,967,640 B2 | 11/2005 | Albert et al. |
| 6,980,196 B1 | 12/2005 | Turner et al. |
| 6,982,178 B2 | 1/2006 | LeCain et al. |
| 6,995,550 B2 | 2/2006 | Jacobson et al. |
| 7,002,728 B2 | 2/2006 | Pullen et al. |
| 7,012,600 B2 | 3/2006 | Zehner et al. |
| 7,012,735 B2 | 3/2006 | Honeyman |
| 7,023,420 B2 | 4/2006 | Comiskey et al. |
| 7,030,412 B1 | 4/2006 | Drzaic et al. |
| 7,030,854 B2 | 4/2006 | Baucom et al. |
| 7,034,783 B2 | 4/2006 | Gates et al. |
| 7,061,166 B2 | 6/2006 | Kuniyasu |
| 7,061,662 B2 | 6/2006 | Chung et al. |
| 7,075,502 B1 | 7/2006 | Drzaic et al. |
| 7,075,703 B2 | 7/2006 | O'Neil et al. |
| 7,106,296 B1 | 9/2006 | Jacobson |
| 7,110,163 B2 | 9/2006 | Webber et al. |
| 7,116,318 B2 | 10/2006 | Amundson et al. |
| 7,116,466 B2 | 10/2006 | Whitesides et al. |
| 7,119,759 B2 | 10/2006 | Zehner et al. |
| 7,119,772 B2 | 10/2006 | Amundson et al. |
| 7,148,128 B2 | 12/2006 | Jacobson |
| 7,163,612 B2 | 1/2007 | Sterling et al. |
| 7,167,155 B1 | 1/2007 | Albert et al. |
| 7,170,670 B2 | 1/2007 | Webber |
| 7,173,752 B2 | 2/2007 | Doshi et al. |
| 7,176,880 B2 | 2/2007 | Amundson et al. |
| 7,177,066 B2 | 2/2007 | Chung et al. |
| 7,190,008 B2 | 3/2007 | Amundson et al. |
| 7,193,625 B2 | 3/2007 | Danner et al. |
| 7,202,847 B2 | 4/2007 | Gates |
| 7,206,119 B2 | 4/2007 | Honeyman et al. |
| 7,223,672 B2 | 5/2007 | Kazlas et al. |
| 7,230,751 B2 | 6/2007 | Whitesides et al. |
| 7,256,766 B2 | 8/2007 | Albert et al. |
| 7,259,744 B2 | 8/2007 | Arango et al. |
| 7,301,693 B2 | 11/2007 | Chaug et al. |
| 7,304,780 B2 | 12/2007 | Liu et al. |
| 7,327,346 B2 | 2/2008 | Chung et al. |
| 7,327,511 B2 | 2/2008 | Whitesides et al. |
| 7,347,957 B2 | 3/2008 | Wu et al. |
| 7,365,733 B2 | 4/2008 | Duthaler et al. |
| 7,382,363 B2 | 6/2008 | Albert et al. |
| 7,388,572 B2 | 6/2008 | Duthaler et al. |
| 7,401,758 B2 | 7/2008 | Liang et al. |
| 7,408,699 B2 | 8/2008 | Wang et al. |
| 7,411,719 B2 | 8/2008 | Paolini, Jr. et al. |
| 7,420,549 B2 | 9/2008 | Jacobson et al. |
| 7,442,587 B2 | 10/2008 | Amundson et al. |
| 7,453,445 B2 | 11/2008 | Amundson |
| 7,471,274 B2 | 12/2008 | Kim |
| 7,492,339 B2 | 2/2009 | Amundson |
| 7,492,497 B2 | 2/2009 | Paolini, Jr. et al. |
| 7,528,822 B2 | 5/2009 | Amundson et al. |
| 7,535,624 B2 | 5/2009 | Amundson et al. |
| 7,551,346 B2 | 6/2009 | Fazel et al. |
| 7,554,712 B2 | 6/2009 | Patry et al. |
| 7,560,004 B2 | 7/2009 | Pereira et al. |
| 7,583,251 B2 | 9/2009 | Arango et al. |
| 7,583,427 B2 | 9/2009 | Danner et al. |
| 7,598,173 B2 | 10/2009 | Ritenour et al. |
| 7,602,374 B2 | 10/2009 | Zehner et al. |
| 7,612,760 B2 | 11/2009 | Kawai |
| 7,636,191 B2 | 12/2009 | Duthaler et al. |
| 7,649,674 B2 | 1/2010 | Danner et al. |
| 7,667,886 B2 | 2/2010 | Danner et al. |
| 7,672,040 B2 | 3/2010 | Sohn et al. |
| 7,679,599 B2 | 3/2010 | Kawai |
| 7,679,813 B2 | 3/2010 | Liang et al. |
| 7,679,814 B2 | 3/2010 | Paolini, Jr. et al. |
| 7,683,606 B2 | 3/2010 | Kang et al. |
| 7,688,497 B2 | 3/2010 | Danner et al. |
| 7,787,169 B2 | 8/2010 | Abramson et al. |
| 7,830,592 B1 | 11/2010 | Sprague et al. |
| 7,839,564 B2 | 11/2010 | Whitesides et al. |
| 7,859,742 B1 | 12/2010 | Chiu et al. |
| 7,880,958 B2 | 2/2011 | Zang et al. |
| 7,893,435 B2 | 2/2011 | Kazlas et al. |
| 7,905,977 B2 | 3/2011 | Qi et al. |
| 7,922,885 B2 | 4/2011 | Adachi et al. |
| 7,952,557 B2 | 5/2011 | Amundson |
| 7,956,841 B2 | 6/2011 | Albert et al. |
| 7,982,479 B2 | 7/2011 | Wang et al. |
| 7,986,450 B2 | 7/2011 | Cao et al. |
| 7,999,787 B2 | 8/2011 | Amundson et al. |
| 8,009,348 B2 | 8/2011 | Zehner et al. |
| 8,049,947 B2 | 11/2011 | Danner et al. |
| 8,072,675 B2 | 12/2011 | Lin et al. |
| 8,120,836 B2 | 2/2012 | Lin et al. |
| 8,125,501 B2 | 2/2012 | Amundson et al. |
| 8,139,050 B2 | 3/2012 | Jacobson et al. |
| 8,149,228 B2 | 4/2012 | Lin et al. |
| 8,159,636 B2 | 4/2012 | Sun et al. |
| 8,159,644 B2 | 4/2012 | Takatori |
| 8,173,000 B1 | 5/2012 | Hadwen et al. |
| 8,174,490 B2 | 5/2012 | Whitesides et al. |
| 8,237,892 B1 | 8/2012 | Sprague et al. |
| 8,243,013 B1 | 8/2012 | Sprague et al. |
| 8,274,472 B1 | 9/2012 | Wang et al. |
| 8,287,708 B2 | 10/2012 | Fan et al. |
| 8,289,250 B2 | 10/2012 | Zehner et al. |
| 8,300,006 B2 | 10/2012 | Zhou et al. |
| 8,314,784 B2 | 11/2012 | Ohkami et al. |
| 8,319,759 B2 | 11/2012 | Jacobson et al. |
| 8,362,488 B2 | 1/2013 | Chaug et al. |
| 8,373,649 B2 | 2/2013 | Low et al. |
| 8,384,658 B2 | 2/2013 | Albert et al. |
| 8,395,836 B2 | 3/2013 | Lin |

(56) References Cited

U.S. PATENT DOCUMENTS

| | | |
|---|---|---|
| 8,419,273 B2 | 4/2013 | Hadwen et al. |
| 8,437,069 B2 | 5/2013 | Lin |
| 8,441,414 B2 | 5/2013 | Lin |
| 8,456,414 B2 | 6/2013 | Lin et al. |
| 8,456,589 B1 | 6/2013 | Sprague et al. |
| 8,462,102 B2 | 6/2013 | Wong et al. |
| 8,514,168 B2 | 8/2013 | Chung et al. |
| 8,525,966 B2 | 9/2013 | Takatori |
| 8,529,743 B2 | 9/2013 | Kim et al. |
| 8,537,105 B2 | 9/2013 | Chiu et al. |
| 8,547,111 B2 | 10/2013 | Hadwen et al. |
| 8,547,628 B2 | 10/2013 | Wu et al. |
| 8,558,783 B2 | 10/2013 | Wilcox et al. |
| 8,558,786 B2 | 10/2013 | Lin |
| 8,558,855 B2 | 10/2013 | Sprague et al. |
| 8,576,162 B2 | 11/2013 | Kang |
| 8,576,164 B2 | 11/2013 | Sprague et al. |
| 8,576,259 B2 | 11/2013 | Lin et al. |
| 8,605,032 B2 | 12/2013 | Liu et al. |
| 8,610,988 B2 | 12/2013 | Zehner et al. |
| 8,654,571 B2 | 2/2014 | John et al. |
| 8,665,206 B2 | 3/2014 | Lin et al. |
| 8,681,191 B2 | 3/2014 | Yang et al. |
| 8,714,780 B2 | 5/2014 | Ho et al. |
| 8,728,266 B2 | 5/2014 | Danner et al. |
| 8,743,077 B1 | 6/2014 | Sprague |
| 8,754,859 B2 | 6/2014 | Gates et al. |
| 8,764,958 B2 | 7/2014 | Wang |
| 8,797,258 B2 | 8/2014 | Sprague |
| 8,797,633 B1 | 8/2014 | Sprague et al. |
| 8,797,636 B2 | 8/2014 | Yang et al. |
| 8,810,525 B2 | 8/2014 | Sprague |
| 8,815,070 B2 | 8/2014 | Wang et al. |
| 8,828,336 B2 | 9/2014 | Hadwen et al. |
| 8,853,645 B2 | 10/2014 | Okada et al. |
| 8,926,065 B2 | 1/2015 | Winger |
| 8,928,562 B2 | 1/2015 | Gates et al. |
| 8,928,641 B2 | 1/2015 | Chiu et al. |
| 8,958,044 B2 | 2/2015 | Takatori |
| 8,976,444 B2 | 3/2015 | Zhang et al. |
| 8,980,075 B2 | 3/2015 | Cheng et al. |
| 8,994,705 B2 | 3/2015 | Jacobson et al. |
| 9,013,394 B2 | 4/2015 | Lin |
| 9,019,197 B2 | 4/2015 | Lin |
| 9,019,198 B2 | 4/2015 | Lin et al. |
| 9,019,318 B2 | 4/2015 | Sprague et al. |
| 9,025,234 B2 | 5/2015 | Lin |
| 9,025,238 B2 | 5/2015 | Chan et al. |
| 9,030,374 B2 | 5/2015 | Sprague et al. |
| 9,082,352 B2 | 7/2015 | Cheng et al. |
| 9,140,952 B2 | 9/2015 | Sprague et al. |
| 9,147,364 B2 | 9/2015 | Wu et al. |
| 9,152,004 B2 | 10/2015 | Paolini, Jr. et al. |
| 9,201,279 B2 | 12/2015 | Wu et al. |
| 9,218,773 B2 | 12/2015 | Sun et al. |
| 9,223,164 B2 | 12/2015 | Lai et al. |
| 9,224,338 B2 | 12/2015 | Chan et al. |
| 9,224,342 B2 | 12/2015 | Sprague et al. |
| 9,224,344 B2 | 12/2015 | Chung et al. |
| 9,230,492 B2 | 1/2016 | Harrington et al. |
| 9,262,973 B2 | 2/2016 | Wu et al. |
| 9,285,648 B2 | 3/2016 | Liu et al. |
| 9,299,294 B2 | 3/2016 | Lin et al. |
| 9,310,661 B2 | 4/2016 | Wu et al. |
| 9,390,066 B2 | 7/2016 | Smith et al. |
| 9,390,661 B2 | 7/2016 | Chiu et al. |
| 9,454,057 B2 | 9/2016 | Wu et al. |
| 9,458,543 B2 | 10/2016 | Hadwen |
| 9,460,666 B2 | 10/2016 | Sprague et al. |
| 9,495,918 B2 | 11/2016 | Harrington et al. |
| 9,501,981 B2 | 11/2016 | Lin et al. |
| 9,513,743 B2 | 12/2016 | Sjodin et al. |
| 9,514,667 B2 | 12/2016 | Lin |
| 9,529,240 B2 | 12/2016 | Paolini, Jr. et al. |
| 9,582,041 B2 | 2/2017 | Cheng et al. |
| 9,620,048 B2 | 4/2017 | Sim et al. |
| 9,620,066 B2 | 4/2017 | Bishop |
| 9,632,373 B2 | 4/2017 | Huang et al. |
| 9,666,142 B2 | 5/2017 | Hung |
| 9,671,635 B2 | 6/2017 | Paolini, Jr. |
| 9,672,766 B2 | 6/2017 | Sjodin |
| 9,691,333 B2 | 6/2017 | Cheng et al. |
| 9,721,495 B2 | 8/2017 | Harrington et al. |
| 9,792,861 B2 | 10/2017 | Chang et al. |
| 9,792,862 B2 | 10/2017 | Hung et al. |
| 9,815,056 B2 | 11/2017 | Wu et al. |
| 9,921,451 B2 | 3/2018 | Telfer et al. |
| 10,037,735 B2 | 7/2018 | Amundson |
| 10,048,563 B2 | 8/2018 | Paolini, Jr. et al. |
| 10,048,564 B2 | 8/2018 | Paolini, Jr. et al. |
| 10,172,388 B2 | 1/2019 | Sears et al. |
| 10,190,743 B2 | 1/2019 | Hertel et al. |
| 10,229,641 B2 | 3/2019 | Yang et al. |
| 10,319,313 B2 | 6/2019 | Harris et al. |
| 10,330,920 B2 | 6/2019 | Brown et al. |
| 10,339,876 B2 | 7/2019 | Lin et al. |
| 10,372,008 B2 | 8/2019 | Telfer et al. |
| 10,446,585 B2 | 10/2019 | Harris et al. |
| 10,466,564 B2 | 11/2019 | Kayal et al. |
| 10,613,407 B2 | 4/2020 | Lin et al. |
| 10,646,454 B2 | 5/2020 | Liu et al. |
| 10,672,350 B2 | 6/2020 | Amundson et al. |
| 2002/0060321 A1 | 5/2002 | Kazlas et al. |
| 2002/0090980 A1 | 7/2002 | Wilcox et al. |
| 2003/0102858 A1 | 6/2003 | Jacobson et al. |
| 2004/0085619 A1 | 5/2004 | Wu et al. |
| 2004/0105036 A1 | 6/2004 | Danner et al. |
| 2004/0119681 A1 | 6/2004 | Albert et al. |
| 2004/0202994 A1 | 10/2004 | Timperman |
| 2004/0246562 A1 | 12/2004 | Chung et al. |
| 2005/0122306 A1 | 6/2005 | Wilcox et al. |
| 2005/0122563 A1 | 6/2005 | Honeyman et al. |
| 2005/0253777 A1 | 11/2005 | Zehner et al. |
| 2006/0255322 A1 | 11/2006 | Wu et al. |
| 2007/0103427 A1 | 5/2007 | Zhou et al. |
| 2007/0176912 A1 | 8/2007 | Beames et al. |
| 2007/0285385 A1 | 12/2007 | Albert et al. |
| 2008/0024429 A1 | 1/2008 | Zehner |
| 2008/0024482 A1 | 1/2008 | Gates et al. |
| 2008/0136774 A1 | 6/2008 | Harris et al. |
| 2008/0154179 A1 | 6/2008 | Cantor et al. |
| 2008/0303780 A1 | 12/2008 | Sprague et al. |
| 2009/0075129 A1 | 3/2009 | Sparks et al. |
| 2009/0098540 A1 | 4/2009 | Baeumner et al. |
| 2009/0122389 A1 | 5/2009 | Whitesides et al. |
| 2010/0177396 A1 | 7/2010 | Lin |
| 2010/0194733 A1 | 8/2010 | Lin et al. |
| 2010/0194789 A1 | 8/2010 | Lin et al. |
| 2010/0225611 A1 | 9/2010 | Lee et al. |
| 2010/0265561 A1 | 10/2010 | Gates et al. |
| 2011/0063314 A1 | 3/2011 | Chiu et al. |
| 2011/0175875 A1 | 7/2011 | Lin et al. |
| 2011/0221740 A1 | 9/2011 | Yang et al. |
| 2011/0292319 A1 | 12/2011 | Cole |
| 2012/0001957 A1 | 1/2012 | Liu et al. |
| 2012/0098740 A1 | 4/2012 | Chiu et al. |
| 2012/0273702 A1 | 11/2012 | Culbertson et al. |
| 2013/0063333 A1 | 3/2013 | Arango et al. |
| 2013/0146459 A1 | 6/2013 | Bazant et al. |
| 2013/0249782 A1 | 9/2013 | Wu et al. |
| 2014/0078024 A1 | 3/2014 | Paolini, Jr. et al. |
| 2014/0192000 A1 | 7/2014 | Hung et al. |
| 2014/0204012 A1 | 7/2014 | Wu et al. |
| 2014/0210701 A1 | 7/2014 | Wu et al. |
| 2014/0240210 A1 | 8/2014 | Wu et al. |
| 2014/0253425 A1 | 9/2014 | Zalesky et al. |
| 2014/0293398 A1 | 10/2014 | Wang et al. |
| 2015/0262255 A1 | 9/2015 | Khajehnouri et al. |
| 2016/0077375 A1 | 3/2016 | Lin |
| 2016/0180777 A1 | 6/2016 | Lin et al. |
| 2016/0312165 A1 | 10/2016 | Lowe, Jr. et al. |
| 2018/0110975 A1 | 4/2018 | Ivanhoff et al. |

(56) References Cited

U.S. PATENT DOCUMENTS

2018/0272114 A1    9/2018  Liu et al.
2018/0284424 A1*  10/2018  Brown .................. G02B 26/005

FOREIGN PATENT DOCUMENTS

| JP | 2008145998 A | 6/2008 |
|---|---|---|
| JP | 2013076739 A | 4/2013 |
| KR | 20070041934 A | 4/2007 |
| TW | 200916823 A | 4/2009 |
| TW | M541866 U | 5/2017 |
| WO | 1999067678 A2 | 12/1999 |
| WO | 2000005704 A1 | 2/2000 |
| WO | 2000036560 A1 | 6/2000 |
| WO | 2000038000 A1 | 6/2000 |
| WO | 2017075295 A1 | 5/2017 |

OTHER PUBLICATIONS

Zhao, Ya-Pu et al., "Fundamentals and Applications of Electrowetting: A Critical Review", Rev. Adhesion Adhesives, vol. 1, No. 1, pp. 114-174 (2013).

Kalsi, S. et. al., "Rapid and sensitive detection of antibiotic resistance on a programmable digital microfluidic platform", Lab on a Chip, Issue No. 14 (2015).

Panchagnula, R et al., "Transdermal delivery of naloxone: skin permeation, pharmacokinetic, irritancy and stability studies", International Journal of Pharmaceutics, 293(1-2), pp. 213-223, Apr. 11, 2005.

Nisar, A. et al., "MEMS-based micropumps in drug delivery and biomedical applications", Sensors and Actuators B: Chemical, vol. 130, Issue 2, pp. 917-942, Mar. 28, 2008.

Choi, Kihwan et al., "Digital Microfluidics", Annu. Rev. Anal. Chem. 5:413-40 (2012).

Dong, Tao et al., "Capacitance Variation Induced by Microfluidic Two-Phase Flow across Insulated Interdigital Electrodes in Lab-On-Chip Devices", Sensors, 15, pp. 2694-2708 (2015).

Geronimo, G. De et al., "Front-end electronics for imaging detectors", Nuclear Instrumentsand Methods in Physics Research A, 471 pp. 192-199, (2001).

Fouillet, Y. et al., "EWOD Digital Microfluidics for Lab on a Chip", International Conference on Nanochannels, Microchannels, and Minichannels, Paper No. ICNMM2006-96020, pp. 1255-1264, (Sep. 2008).

Korean Intellectual Property Office, PCT/US2019/056173, International Search Report and Written Opinion, Jan. 31, 2020.

European Patent Office, "Extended European Search Report", EP Appl. No. 19874198.5, Jun. 14, 2022.

* cited by examiner

DIGITAL MICROFLUIDIC DELIVERY DEVICE

RELATED APPLICATIONS

This application is a continuation of U.S. patent application Ser. No. 16/601,641, filed Oct. 15, 2019, which claims priority to U.S. Provisional Patent Application No. 62/745,718, filed Oct. 15, 2018. All patents, publications, and pending applications disclosed herein are incorporated by reference in their entireties.

BACKGROUND

Digital microfluidic devices use independent electrodes to propel, split, and join droplets in a confined environment, thereby providing a "lab-on-a-chip." Digital microfluidic devices are alternatively referred to as electrowetting on dielectric, or "EWoD," to further differentiate the method from competing microfluidic systems that rely on electrophoretic flow and/or micropumps. A 2012 review of the electrowetting technology was provided by Wheeler in "Digital Microfluidics," *Annu. Rev. Anal. Chem.* 2012, 5:413-40, which is incorporated herein by reference in its entirety. The technique allows sample preparation, assays, and synthetic chemistry to be performed with tiny quantities of both samples and reagents. In recent years, controlled droplet manipulation in microfluidic cells using electrowetting has become commercially viable; and there are now products available from large life science companies, such as Oxford Nanopore.

Most of the literature reports on EWoD involve so-called "passive matrix" devices (a.k.a. "segmented" devices), whereby ten to twenty electrodes are directly driven with a controller. While segmented devices are easy to fabricate, the number of electrodes is limited by space and driving constraints. Accordingly, it is not possible to perform massive parallel assays, reactions, etc. in passive matrix devices. In comparison, "active matrix" devices (a.k.a. active matrix EWoD, a.k.a. AM-EWoD) devices can have many thousands, hundreds of thousands or even millions of addressable electrodes. The electrodes are typically switched by thin-film transistors (TFTs) and droplet motion is programmable so that AM-EWoD arrays can be used as general purpose devices that allow great freedom for controlling multiple droplets and executing simultaneous analytical processes.

Figure 1:
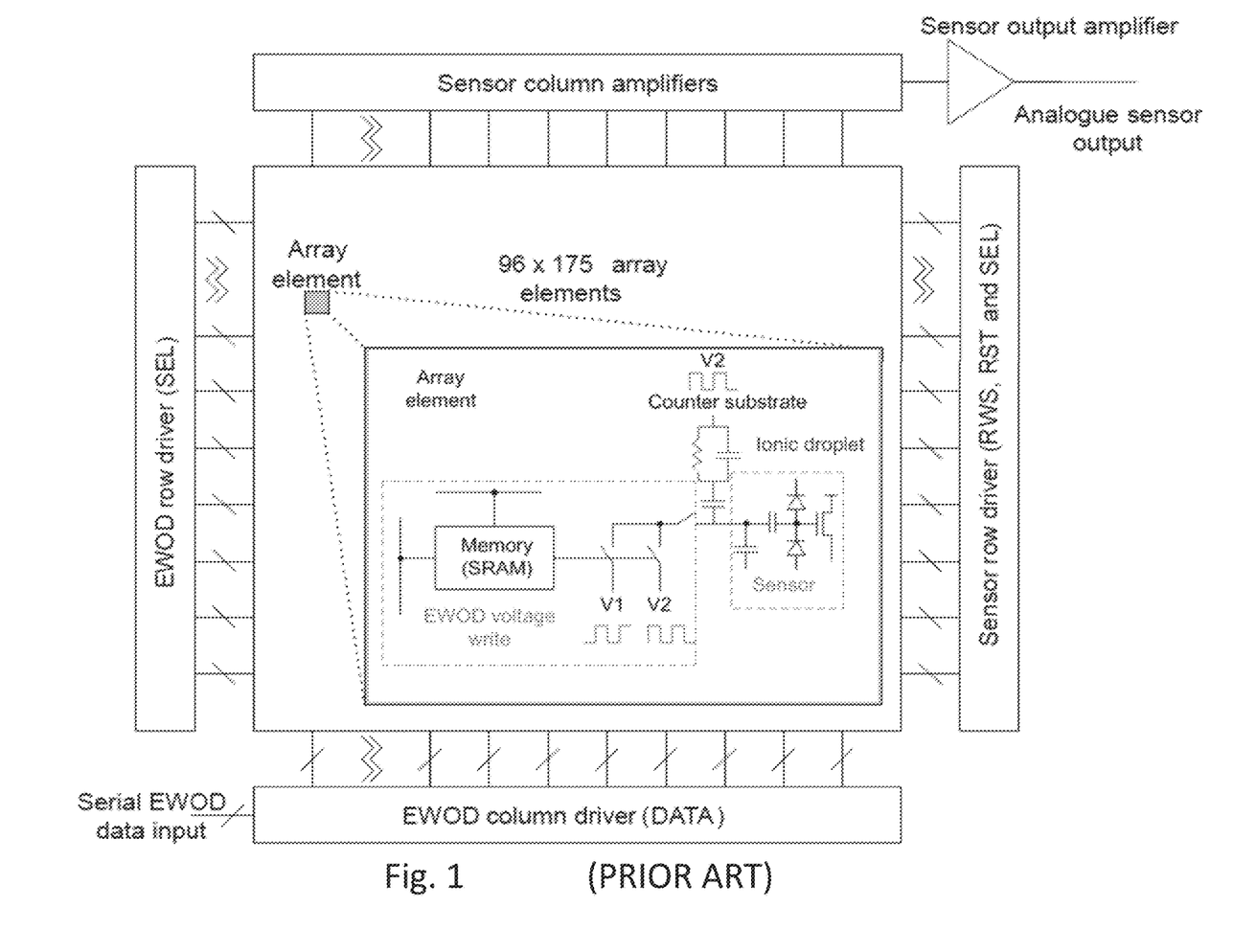
FIG. 1 shows a prior art EWoD device including both propulsion and sensing on the same active matrix.

Because of the restrictive requirements on the electric field leakage, most advanced AM-EWoD devices are constructed from polycrystalline silicon (a.k.a. polysilicon, a.k.a. poly-Si). However, polysilicon fabrication is substantially more expensive than amorphous silicon fabrication, i.e., the type used in mass-produced active matrix TFTs for the LCD display industry. Polysilicon fabrication processes are more expensive because there are unique handling and fabrication steps for working with polysilicon. There are also fewer facilities worldwide that are configured to fabricate devices from polysilicon. However, because of the improved functionality of polysilicon, Sharp Corporation has been able to achieve AM-EWoD devices that include propulsion, sensing, and heating capabilities on a single active matrix. See, e.g., U.S. Pat. Nos. 8,419,273, 8,547,111, 8,654,571, 8,828,336, 9,458,543, all of which are incorporated herein by reference in their entireties. An example of a complex poly-Si AM-EWoD is shown in FIG. 1.

Transdermal delivery of bioactive materials is well-established technology. In the most straightforward embodiments the biologically-active component (typically a molecule having molecular weight below about 1000) is incorporated into a polymeric matrix or gel that is placed into contact with a patient's skin. Penetration of the molecule occurs by passive diffusion, often over a period of several hours. The initiation of drug delivery is by application of the patch to the skin. In the current state of the art it is difficult to modulate the rate of delivery of the active ingredient, however, from one particular patch.

SUMMARY

The invention addresses this need by providing a low power transdermal delivery system whereby the active molecules can be loaded with a digital microfluidic platform and released on demand. Additionally, as described below, the invention provides a system for delivering varying concentrations of active molecules from the same delivery system at different times, and for delivering multiple drugs at the same, or different, times from the same patch.

The invention works by holding an active (i.e. a drug) in a reservoir until it is needed and then it is moved to a porous diffusion layer (e.g., a drug delivery gel) that is in contact with the skin. In one aspect, the invention is an active molecule delivery system comprising a first substrate, a second substrate, a spacer, a porous diffusion layer and a controller. The first substrate includes a plurality of driving electrodes, a dielectric layer covering the plurality of electrodes, and a first hydrophobic layer covering the dielectric layer. The second substrate includes a common electrode, and a second hydrophobic layer covering the common electrode. The spacer separates the first and second substrates and creates a microfluidic region between the first and second substrates. The porous diffusion layer is coupled to the first substrate on a side of the substrate opposed to the first hydrophobic layer, and the first substrate comprises a passage providing fluidic communication between the hydrophobic layer and the porous diffusion layer. The controller is operatively coupled to the driving electrodes and configured to provide a voltage gradient between at least two driving electrodes. The porous diffusion layer may be constructed from a variety of materials, such acrylate, methacrylate, polycarbonate, polyvinyl alcohol, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polybutylene, polypropylene, polyisobutylene, or polystyrene. Typically, the reservoir has a volume greater than 100 nL, and the porous diffusion layer has an average pore size of between 1 nm and 100 nm. In some embodiments, a device includes a plurality of passages. In some embodiments, the passages include wicking materials such as capillary tubes or fibers. In some embodiments, the porous diffusion layer is coupled to a subject with a biocompatible adhesive.

Typically, the active molecule is a pharmaceutical compound; however, systems of the invention can be used to deliver hormones, nutraceuticals, proteins, nucleic acids, antibodies, or vaccines. The invention may include a plurality of reservoirs and the device may be configured to mix components prior to administering the components. For example, it is possible to have different reservoirs within the same device containing different mixtures or similar mixtures having different concentrations. For example, a system may include a first reservoir containing a mixture of first active molecules and a second reservoir containing a mixture of second active molecules, or a system may include a first reservoir containing active molecules at a first concentration and a second reservoir containing the same active molecules at a second concentration. In other embodiments, the system may include a first reservoir containing a mixture of active molecules and a second reservoir containing an adjuvant and/or a skin penetrant. Other combinations of active molecules, agents, and concentrations will be evident to one of skill in the art.

The invention additionally includes a controller for controlling an active molecule delivery system. This controller includes an active molecule delivery system as described above, that is, including a mixture of an active molecule dispersed in a first charged phase and a second phase that is oppositely charged or uncharged and immiscible with the first phase, or a mixture of an active molecule and charged particles. The controller may also include a switch configured to interrupt flow from the voltage source to the active molecule delivery system. The switch may be a mechanical switch or a digital switch, and the controller may include a processor for controlling the switch. In some embodiments, the controller will include a wireless receiver and a wireless transmitter, thereby allowing the controller to be interfaced with a device, such as a smart phone, docking station, smart watch, fitness tracker, etc.

Devices of the invention can be used to deliver active molecules to the skin of a subject. For example, using a device of the invention a the porous diffusion layer can be coupled to the skin of a subject, a solution comprising an active molecule can be moved from a driving electrode to the first passage providing fluidic communication between the hydrophobic layer and the porous diffusion layer, and an active molecule allowed to pass from the porous diffusion layer to the skin of the subject. In some embodiments, the active is held in a first reservoir in fluidic communication with the plurality of driving electrodes, and the solution comprising an active molecule is held in the reservoir until the solution comprising an active molecule is required for delivery. In some embodiments, a device has two separate reservoirs and a mixing area and an active molecule is delivered to a patient. The first reservoir includes a first precursor solution, the second reservoir includes a second precursor solution, and the delivery function includes mixing the first precursor molecule with the second precursor molecule to create a mixture and moving the mixture to a passage providing fluidic communication between the hydrophobic layer and the porous diffusion layer.

BRIEF DESCRIPTION OF DRAWINGS

FIG. 5 shows step-by-step (bottom to top) dispensing a solution including an active molecule, moving the droplets toward passages, movement to the passages, and dispensing the droplets into the porous diffusion layer.

DETAILED DESCRIPTION

The invention provides an active molecule delivery system whereby active molecules can be released on demand and/or a variety of different active molecules can be delivered from the same system and/or different concentrations of active molecules can be delivered from the same system. The invention is well-suited for delivering pharmaceuticals to patients transdermally, however the invention may be used to deliver active ingredients to animals, generally. The active delivery system includes a plurality of reservoir(s), wherein the reservoir(s) are filled with a medium for delivering the active molecules. In some embodiments the medium includes active molecules dispersed in a first charged phase as well as a second phase that is oppositely charged or uncharged and immiscible with the first phase.

One molecule of interest for transdermal delivery is naloxone, a competitive opioid receptor antagonist that is used to prevent or reduce the effects of overdose of opioid narcotics. Naloxone is poorly absorbed when taken by mouth and is typically administered by injection or by means of nasal spray. Unfortunately, the effects of the drug diminish after less than about an hour, requiring the administration of several doses to maintain therapeutic levels over long periods. Prior work has suggested, however, that use of a transdermal patch of about 40 $cm^2$ in area may be able maintain useful plasma concentrations of naloxone over a period of about 4-48 hours. See, e.g., Panchagula, R., Bokalial, R., Sharma, P. and Khandavilli, S., *International Journal of Pharmaceutics*, 293 (2005), 213-223. Thus, a combination of an initial injected dose with a longer-acting transdermal infusion might provide a practical means to maintain a therapeutic concentration of naloxone while avoiding subjecting a patient to multiple injections.

Military and civilian first responders, including law-enforcement personnel, face the possibility of exposure to high concentrations of opioid narcotics in dangerous situations in which access to conventional medical care may be impossible. Ideally, they would be able to self-administer an initial bolus of naloxone (or a similar drug) and at the same time be able to trigger longer-term release of a maintenance dose. It might in some situations even be necessary that release of the drug be triggered remotely, especially when the affected individual's ability to function independently has been compromised. In these situations it would be preferred to use a pre-applied transdermal patch in a state in which the drug to be delivered is in some way unavailable. A triggering event would release the drug, allowing it to begin to diffuse through the skin. Of course, delivery device are not limited to these examples and can be used to deliver, e.g., hormones, nutraceuticals, proteins, nucleic acids, antibodies, or vaccines.

Figure 2:
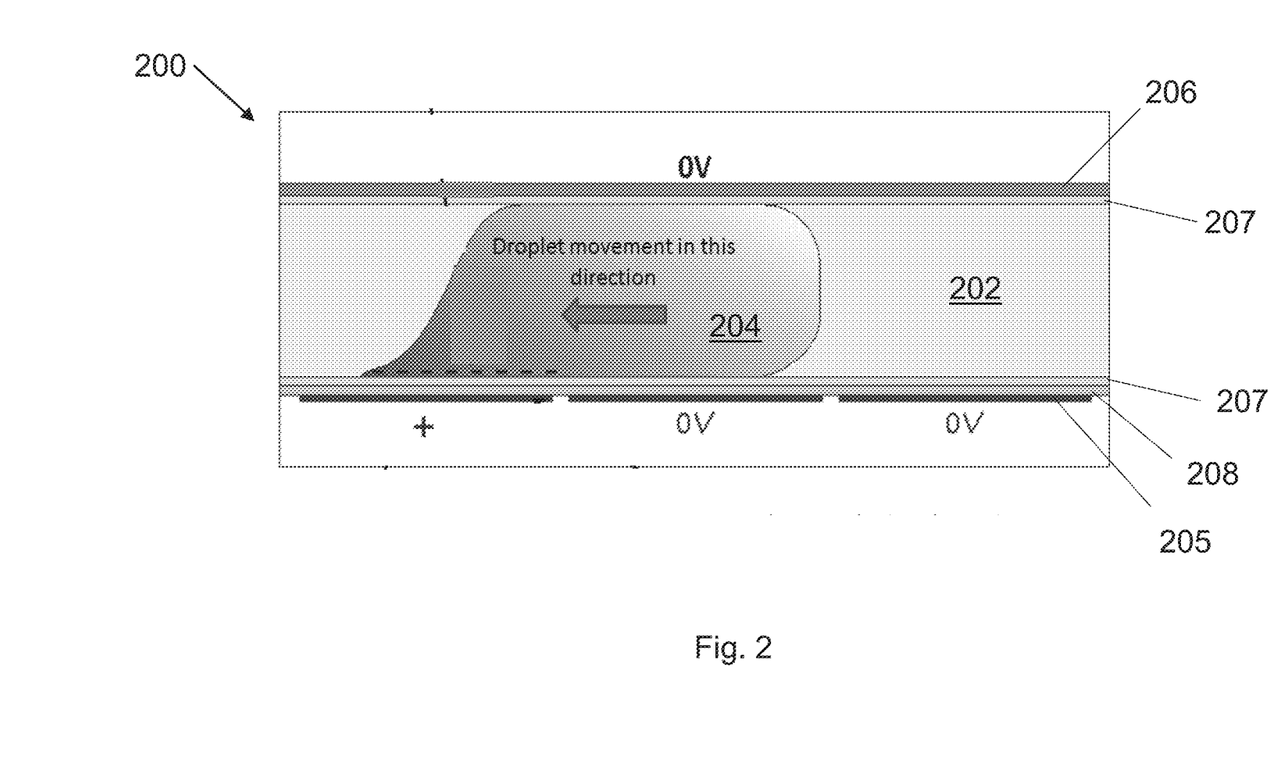
FIG. 2 depicts the movement of an aqueous-phase droplet between adjacent electrodes by providing differing charge states on adjacent electrodes.

Devices of the invention function by moving aqueous droplets of actives using electrowetting on dielectric (EWoD). The fundamental operation of an EWoD device is illustrated in the sectional image of FIG. 2. The EWoD 200 includes a cell filled with an oil 202 and at least one aqueous droplet 204. The cell gap is typically in the range 50 to 200 µm, but the gap can be larger. In a basic configuration, as shown in FIG. 2, a plurality of driving electrodes 205 are disposed on one substrate and a singular top electrode 206 is disposed on the opposing surface. The cell additionally includes hydrophobic coatings 207 on the surfaces contacting the oil layer, as well as a dielectric layer 208 between the driving electrodes 205 and the hydrophobic coating 207. (The upper substrate may also include a dielectric layer, but it is not shown in FIG. 2). The hydrophobic layer prevents the droplet from wetting the surface. When no voltage differential is applied between adjacent electrodes, the droplet will maintain a spheroidal shape to minimize contact with the hydrophobic surfaces (oil and hydrophobic layer). Because the droplets do not wet the surface, they are less likely to contaminate the surface or interact with other droplets except when that behavior is desired.

While it is possible to have a single layer for both the dielectric and hydrophobic functions, such layers typically require thick inorganic layers (to prevent pinholes) with resulting low dielectric constants, thereby requiring more than 100V for droplet movement. To achieve low voltage actuation, it is better to have a thin inorganic layer for high capacitance and to be pinhole free, topped by a thin organic hydrophobic layer. With this combination, it is possible to have electrowetting operation with voltages in the range +/−10 to +/−50V, which is in the range that can be supplied by conventional TFT controllers.

When a voltage differential is applied between adjacent electrodes, the voltage on one electrode attracts opposite charges in the droplet at the dielectric-to-droplet interface, and the droplet moves toward this electrode, as illustrated in FIG. 2. The voltages needed for acceptable droplet propulsion depend on the properties of the dielectric and hydrophobic layers. AC driving is used to reduce degradation of the droplets, dielectrics, and electrodes by various electrochemistries. Operational frequencies for EWoD can be in the range 100 Hz to 1 MHz, but lower frequencies of 1 kHz or lower are preferred for use with TFTs that have limited speed, of operation.

Figure 3:
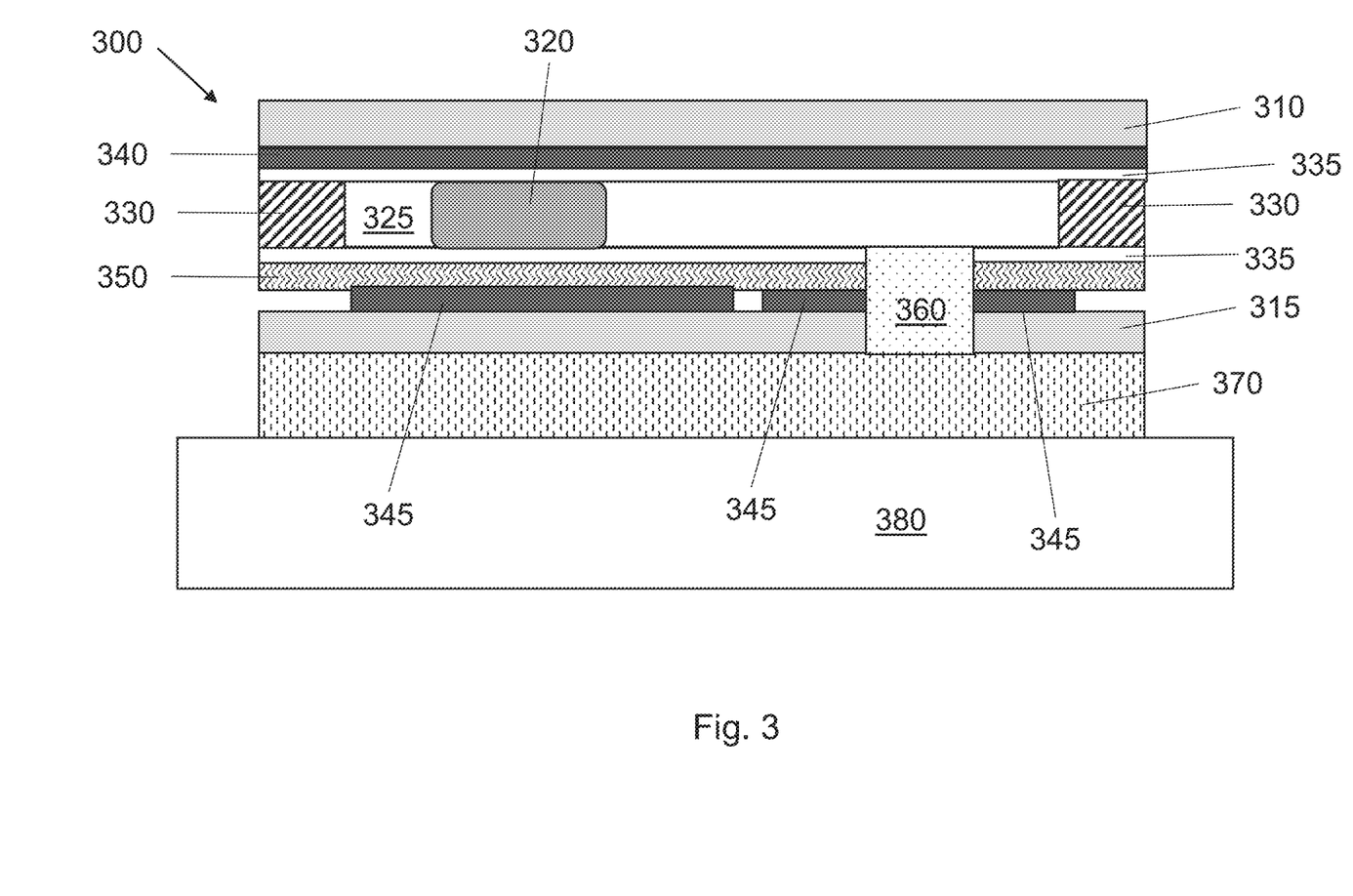
FIG. 3 depicts a cross-section of the invention when the device is in an "off state" that is, the active has not been loaded.

FIG. 3 shows the principle of operation of an active molecule delivery device 300 of the invention in cross-sectional form (not to scale) when disposed upon skin 380. The device 300 is constructed on one or more substrates 310/315, which may be a flexible substrate. A common electrode 340 is spaced from a driving electrode 345 by a spacer 330. The active molecule (drug) to be delivered is dissolved in a water drop 320 suspended in an incompatible solvent 325 (for example, a hydrocarbon, silicone, or fluorinated organic oil). As discussed above, application of appropriate voltages to the common electrode 340 and the driving electrodes 345 can be used to move the water drop 320 laterally toward the passage 360 which is coupled to the porous diffusion layer 370 (from left to right). To facilitate movement of the water drop 320, a hydrophobic layer 335 is provided below the common electrode 340 and above the driving electrodes 345. A dielectric layer 350 is intermediate between the hydrophobic layer 335 and the driving electrodes 345.

Figure 4:
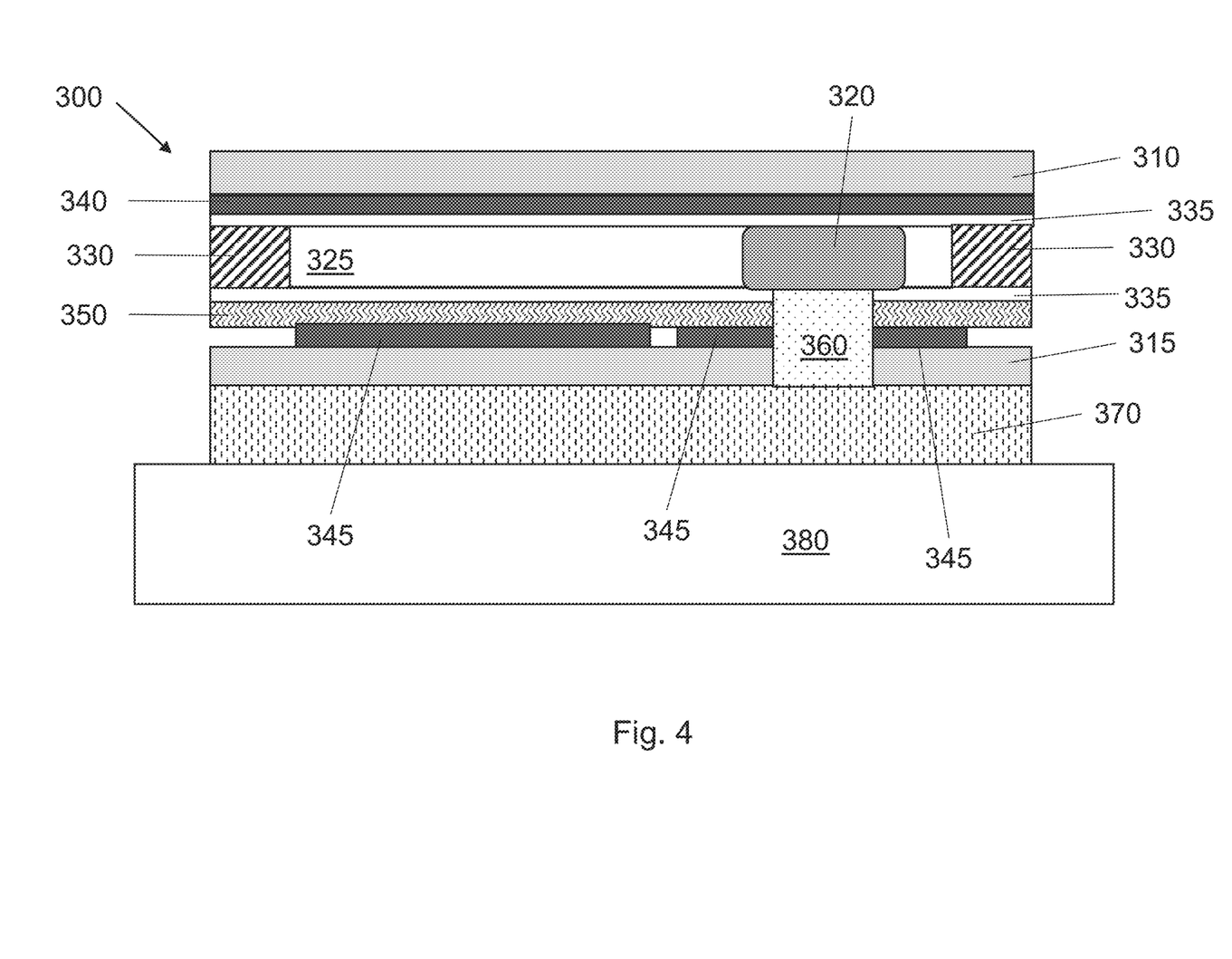
FIG. 4 depicts a cross-section of the invention when the device is in an "on state" that is, the active has been loaded.

A device of the invention includes one or more passages 360 (i.e., a channel in the z-direction), either through or adjacent to a driving electrode 345. When a water drop 320 is positioned over such a passage 360, as shown in FIG. 4, the active molecules can move through the passage 360 to the porous diffusion layer 370 that is in contact with the delivery surface, e.g., a patient's skin 380. At this location, diffusional contact is established between the water droplets 320 and the porous diffusion layer 370 that is in contact with the skin 380. Typically, the passage 360 will include structures to facilitate movement of the solvent and active mixture from the hydrophobic surface 335 to the porous diffusion layer 370. For example, the passage may include materials that move hydrophilic materials through capillary action, such as wicking fibers, cellulose, or cotton. Such materials may be coated with an additional hydrophobic coating to facilitate movement of the aqueous solution from the el ectrowetting surface to the porous diffusion layer 370. In some embodiments, a biocompatible adhesive (not shown) may laminated to the porous diffusion layer. The biocompatible adhesive will allow active molecules to pass through while keeping the device immobile on a user. Suitable biocompatible adhesives are available from 3M (Minneapolis, MN).

Figure 5:
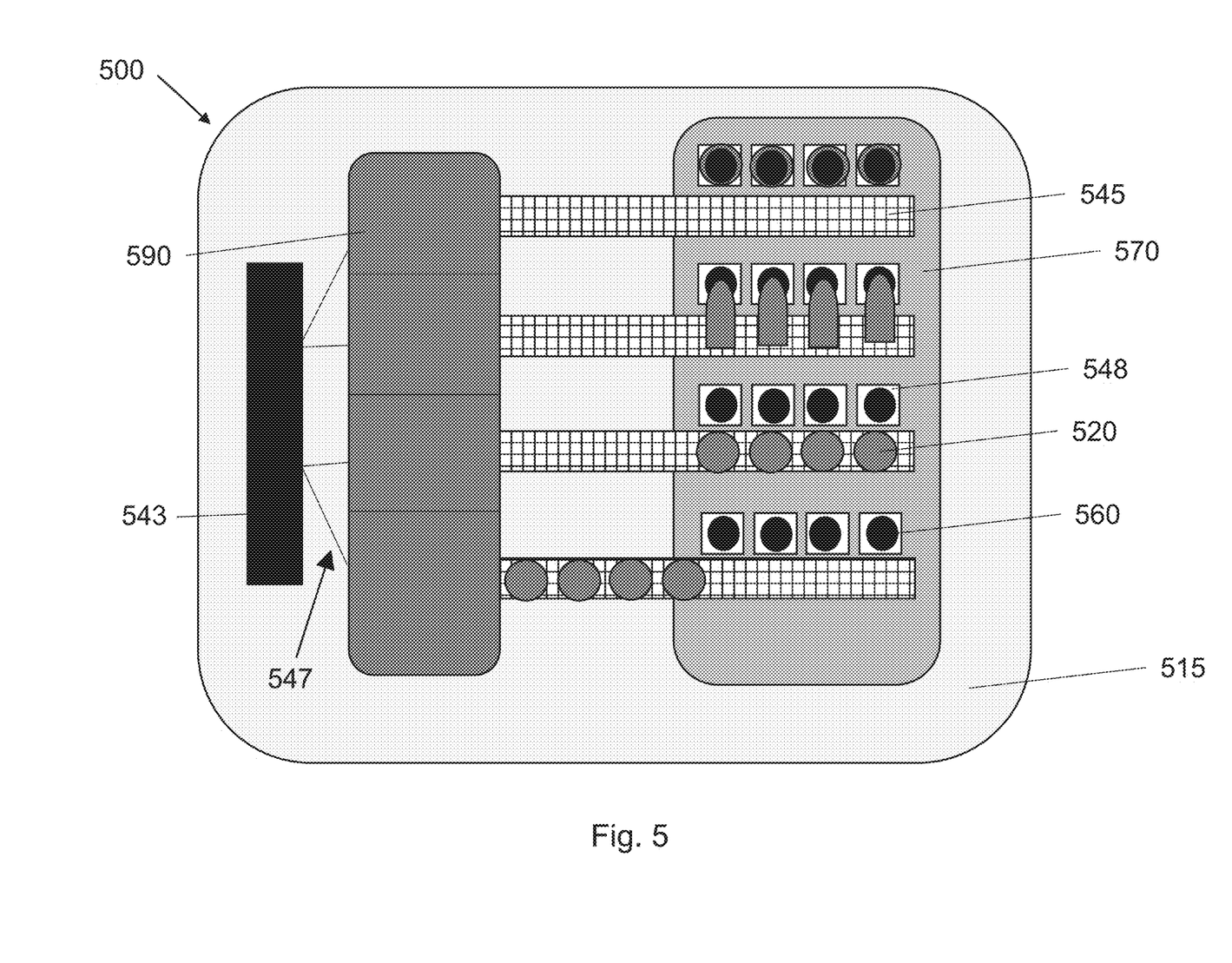
FIG. 5 is a plan view of a device of the invention including a reservoir of active material, driving electrodes, passages and a porous diffusion layer.

FIG. 5 shows a top view of an embodiment of an active molecule delivery device 500 of the invention as if the top electrode and the top substrate have been removed. The device 500 includes a substrate 515, driving electrodes 545, passages 560, and a porous diffusion layer 570. The device additionally includes a controller 543 that is coupled to the driving electrodes 545 with traces 547. As shown in FIG. 5 a hydrophilic liquid containing a target molecule (drug) to be delivered is located in a reservoir 590, i.e., a region of the device remote from the porous diffusion layer that contacts the skin.

The sequence of delivery of a solution including an active molecule is illustrated in FIG. 5 running from the bottom driving electrodes to the top driving electrodes. Initially, droplets 520 are snapped off from the reservoir 590 thereby determining the dosage that will be delivered (concentration×volume×number of droplets). The droplets 520 are advanced until they are adjacent one or more passages 560, whereupon an auxiliary driving electrode 548 that surrounds the passage 560 is used to move the droplets 520 above the passages 560 using orthogonal electrowetting. Due to the wicking action of the passage 560, the droplets 520 will move into and through the passages 560 whereupon they are delivered to the porous diffusion layer 570 below. Accordingly, the active ingredients in the reservoir(s) 590 can be moved into the porous diffusion layer.

Figure 6:
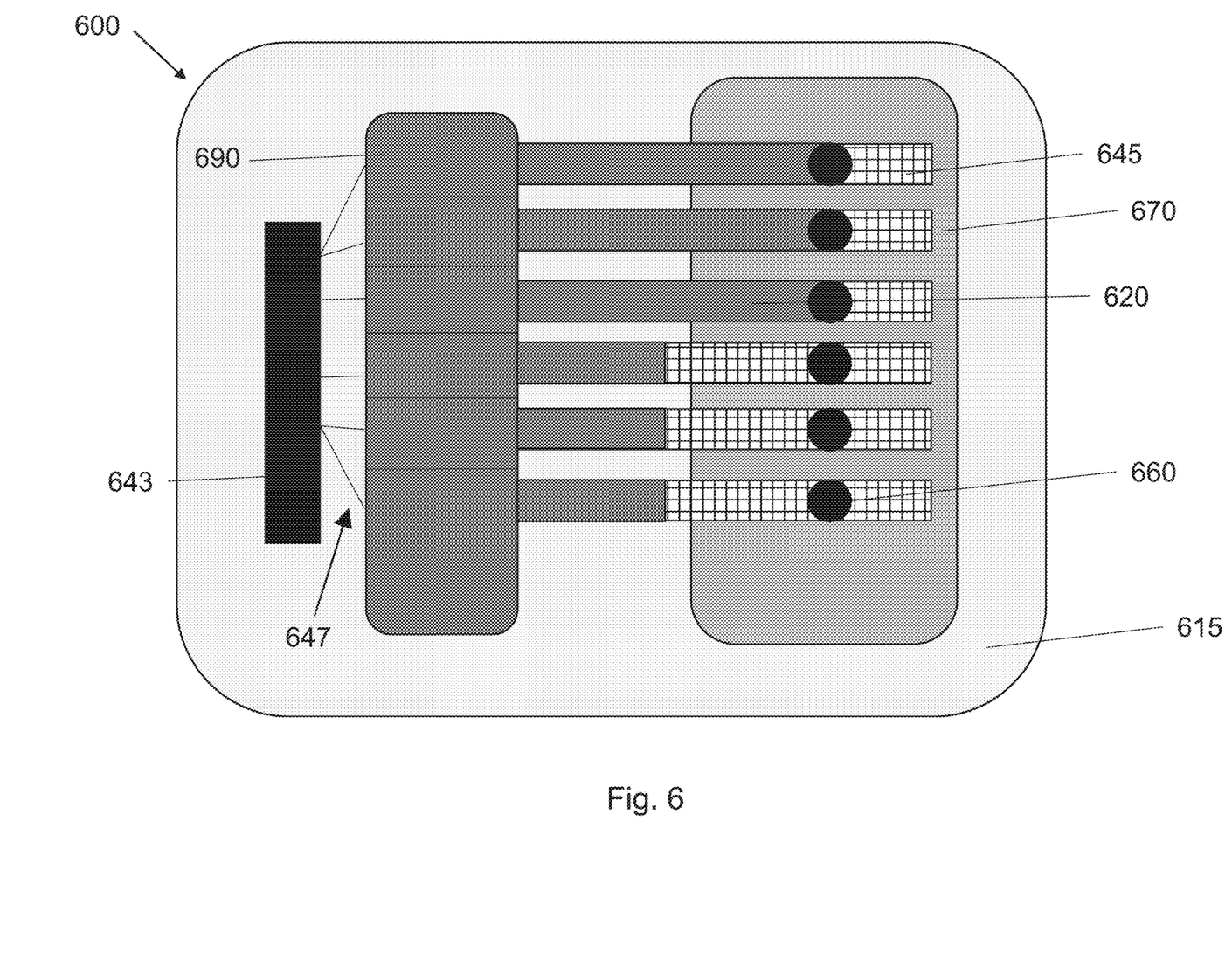
FIG. 6 illustrates a device of the invention wherein each passage is coupled to only a single reservoir. In some embodiments, each reservoir contains a different concentration of active molecules, thereby allowing the dosage to be dynamically controlled.

It is possible to imagine numerous different arrangements of driving electrodes 545 with respect to the passages 560. In a second embodiment, illustrated in FIG. 6, electrowetting forces are used to withdraw fluid 620 from the reservoir 690 and transfer it directly to a passage 660. The device 600 includes a substrate 615, driving electrodes 645, passages 660, and a porous diffusion layer 670. The device additionally includes a controller 643 that is coupled to the driving electrodes 645 with traces 647. No orthogonal motion is needed in FIG. 6, however. Capillary forces, provided by suitable materials between the driving electrodes 645 and the porous diffusion layer 670, withdraw fluid 620 from the reservoir 690. While the fluid 620 is shown to be continuous, it is to be understood that the fluid can be delivered in droplets as in FIG. 5. As shown in FIG. 6, each passage 660 is coupled to a unique reservoir 690. This allows each reservoir to act as a single dose, thereby reducing the complexity of the system, e.g., whereby a specific number of droplets of a specific volume of a specific dosage must be snapped off and delivered. For example, a device 600 may include seven identical reservoirs and the controller 643 configured to administer the contents of one reservoir each morning for seven consecutive days. Alternatively, different reservoirs 690 may each contain different concentrations of the same active so that, for example, a subject can receive a first stronger dose of the active and then receive one or more lower concentration maintenance doses during the day. Such a device may be particularly well suited for delivering hormones.

Figure 7:
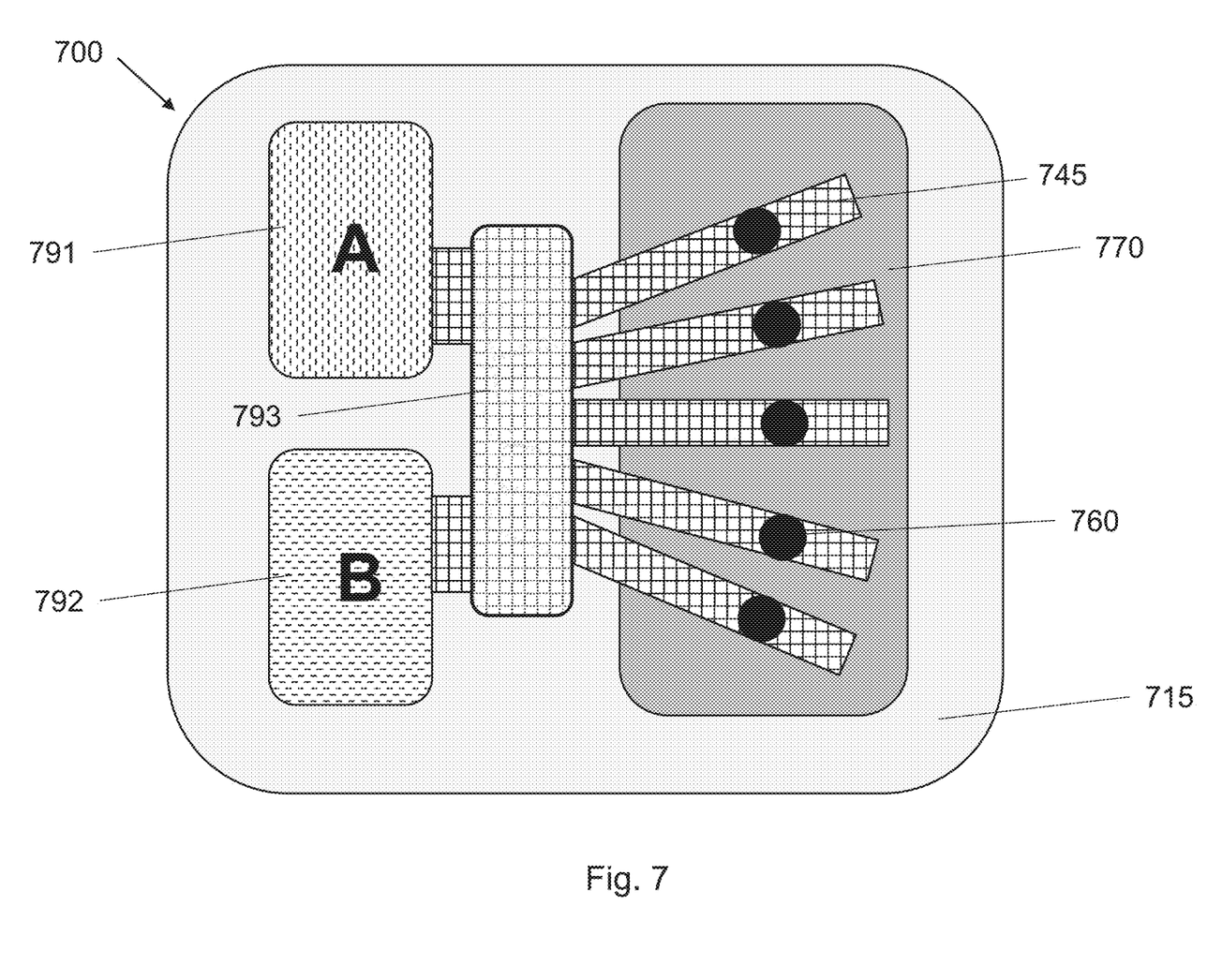
FIG. 7 illustrates a device of the invention whereby two different reservoirs are coupled to a mixing area whereby two components "A" and "B" can be mixed prior to delivery to the porous diffusion layer.

Another embodiment of the invention is shown in FIG. 7, where the device 700 includes a substrate 715, driving electrodes 745, passages 760, and a porous diffusion layer 770. While a controller is not shown, it is understood that a controller is needed to coordinate functions of the driving electrodes 745. FIG. 7 illustrates that it is possible to do reactions "on chip" before delivering an active molecule. As shown in FIG. 7, a first reservoir "A" 791 and a second reservoir "B" 792 are both in fluidic communication with a mixing area 793. A first precursor molecule can be contained in a first solution in the first reservoir 791 while a second precursor molecule can be contained in a second solution in the second reservoir 792. Prior to administering an active, the first solution and the second solution are brought to the mixing area 793 where they are allowed to mix to create the target active, which is then delivered to the porous diffusion layer 770 in a method described above.

There are many advantages to a device 700 with the ability to mix precursors prior to delivering a target active to the porous diffusion layer 770. For example, the first precursor may be a sensitive biologic, such as an antibody or an oligonucleotide that must be stabilized for storage in a solution that is not suitable for delivery through the porous diffusion layer. Accordingly, when it is appropriate to deliver the biologic, an amount is transferred from the first reservoir 791 to the mixing area 793 where the biologic can be activated, cleaned, or targeted for delivery (e.g., via conjugation with promoters, markers, or other target specific molecules). Such configurations may greatly increase the shelf life of the biologics and they may allow a patient to avoid having to go to a clinic to have the biologic delivered via intravenous injection. In other alternatives, the first and second precursors may be prodrugs that combine to create an opioid. Using a device of the invention, it may be possible to prevent illegal opioid administration because only users having the device and appropriate security authorization could combine the precursors to create the opioid.

The system of FIG. 7 may also be suitable for delivering so-called "drug cocktails" that include active molecules that deactivate each other over time and typically must be administered in a clinic, e.g., a chemotherapy clinic. The system of FIG. 7 may also be used to deliver, e.g., a patient's own cells, antibodies, etc. In such embodiments, the patient's own biological materials may be held in a first reservoir and when it is appropriate to deliver the therapeutic, the patient's own biological materials are moved to the mixing area where they are combined with another active ingredient prior to being delivered to the porous diffusion layer.

The controller 543, 643, 743, may comprise a battery and electronics required to initiate the electrowetting motion, and means to communicate with the outside world such as appropriate electronics/antenna, etc. In preferred arrangements, it will not be possible to transfer drops of water containing the drug to the passages without applying electrical signals. This will ensure that the unactivated patch may be subjected to a variety of stresses (mechanical, thermal, etc.) without releasing the active ingredient.

In one embodiment, a device of the invention can be used to deliver naloxone (NARCAN™). The device would deliver about 20-100 mg of the drug from the reservoir to the porous diffusion area. Assuming a near-saturated concentration of active (e.g., naloxone) in water in the reservoir of 50 mg/mL, the volume of drops required to be delivered would be about 400-2000 μL, which is within the capability of the devices. In other embodiments, devices of the invention can be used to deliver opioids, e.g., hydromorphone, hydrocodone, fentanyl, methadone, or oxycodone. Devices of the invention may be used to deliver stimulants such as nicotine, steroids (e.g., prednisone), and hormones (e.g., epinephrine).

Figure 8:
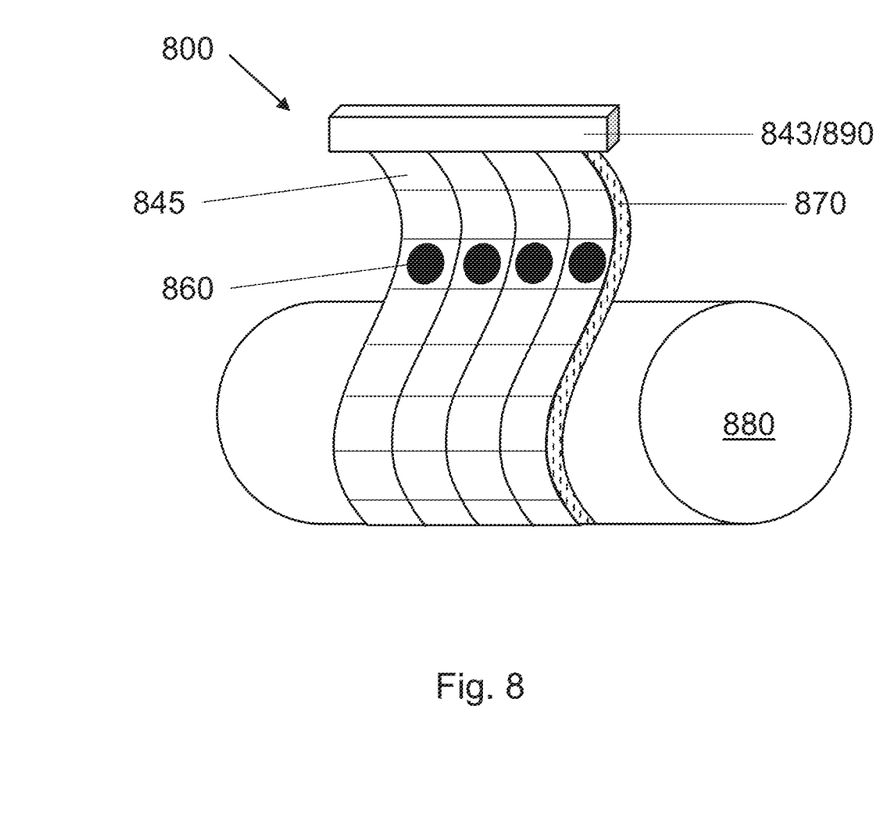
FIG. 8 illustrates a delivery device of the invention wherein the driving electrodes are flexible, thereby allowing the delivery device to be wrapped around a limb, e.g., an arm or a leg.

In some embodiments, a device of the invention can be made to be flexible so that the device can deployed on a curved surface 880 and/or integrated into a flexible package to improve user comfort and compliance. An embodiment of such a device 800 is shown in FIG. 8, whereby flexible drive electrodes 845 are coupled to a porous diffusion layer 870 and passages 860 provide fluidic communication between the drive electrodes 845 and the porous diffusion layer 870. As shown in FIG. 8, the controller 843 and the reservoir 890 may be combined into the same housing. In an embodiment, the device 800 may take the shape of a wristband, whereby the device 800 may be additionally augmented with decorative designs to hide that the device 800 is, in fact, for delivering drugs transdermally.

Advanced embodiments of an active molecule delivery system will include circuitry to allow the active molecule delivery system to be controlled wirelessly with a secondary device, such as a smart phone or smart watch. With such improvements, a user can control, for example, the type of active molecule that is delivered and the amount that is delivered. Using an application on, e.g., a smart phone or watch, it may be possible to program the device to modify the amount of active molecule delivered based upon the time of day. In other embodiments, the device may be operatively coupled with biometric sensors, e.g., a fitness tracker or heart rate monitor, whereby the application causes the dosage to be turned off if, e.g., the pulse rate of the user exceeds a preset threshold. Other embodiments may couple, e.g., a readout from a glucose monitor to the device to allow for automatic delivery of insulin when a patient is outside of their desired blood glucose level.

When desired, devices of the invention can be activated and/or controlled remotely. For example, NFC, Bluetooth, WIFI, or other wireless communication function may be used to activate a device and cause the agent to be administered. Furthermore, the same wireless communication may be used to monitor the performance of the device, e.g., the percentage and area for all of the reservoir(s) at different driving status is known, which means all of the usage data will be available to a provider or therapist, including when the patch is activated and what amount of active is administered. For the "programmable" feature, because each reservoir can be turned independently, the overall release profile of the device can be programmed by driving differing concentrations of actives or different actives from different reservoirs at different times. Additionally, patient compliance is also good because the smart device that is used to activate the patch can also communicate with doctors remotely for data sharing.

It will be apparent to those skilled in the art that numerous changes and modifications can be made in the specific embodiments of the invention described above without departing from the scope of the invention. Accordingly, the whole of the foregoing description is to be interpreted in an illustrative and not in a limitative sense.

The invention claimed is:

1. An active molecule delivery system comprising:
   a first substrate comprising:
      a plurality of driving electrodes,
      a dielectric layer covering the plurality of electrodes, and
      a first hydrophobic layer coveting the dielectric layer;
   a second substrate comprising:
      a common electrode,
      a second hydrophobic layer covering the common electrode;
   a spacer separating the first and second substrates and creating a microfluidic region between the first and second substrates;
   a plurality of reservoirs in fluidic communication with the plurality of driving electrodes;
   a porous diffusion layer coupled to the first substrate on a side of the substrate opposed to the first hydrophobic layer;
   a plurality of passages providing fluidic communication between the hydrophobic layer and the porous diffusion layer, wherein each of the plurality of reservoirs is in fluidic communication with only one passage, thereby providing an exclusive pathway of fluidic communication between each of the plurality of reservoirs and the porous diffusion layer; and
   a controller operatively coupled to the driving electrodes and configured to provide a voltage gradient between at least two driving electrodes.

2. The active molecule delivery system of claim 1, wherein each driving electrode is coupled to a thin-film-transistor.

3. The active molecule delivery system of claim 1, wherein the driving electrodes are flexible.

4. The active molecule delivery system of claim 1, wherein the plurality of passages include capillary tubes or wicking fibers.

5. The active molecule delivery system of claim 4, wherein the capillary tubes or wicking fibers are coated with a hydrophobic coating.

6. The active molecule delivery system of claim 1, wherein the porous diffusion layer comprises acrylate, methacrylate, polycarbonate, polyvinyl alcohol, cellulose, poly (N-isopropylacrylaimed) (PNIPAAm), poly(lactic-co-glycolic acid) (PLGA), polyvinylidene chloride, acrylonitrile, amorphous nylon, oriented polyester, terephthalate, polyvinyl chloride, polyethylene, polybutylene, polypropylene, polyisobutylene, or polystyrene.

7. The active molecule delivery system of claim 1, further comprising a biocompatible adhesive in contact with the porous diffusion layer.

8. A method for delivering an active molecule to the skin of a subject, comprising:
   providing an active molecule delivery system including:
      a first substrate comprising:
         a plurality of driving electrodes;
         a dielectric layer covering the plurality of electrodes, and
         a first hydrophobic layer covering the dielectric layer;
      a second substrate comprising:
         a common electrode,
         a second hydrophobic layer covering the common electrode;
      a spacer separating the first and second substrates and creating a microfluidic region between the first and second substrates;
      a plurality of reservoirs in fluidic communication with the plurality of driving electrodes;
      a porous diffusion layer coupled to the first substrate on a side of the substrate opposed to the first hydrophobic layer;
      a plurality of passages providing fluidic communication between the hydrophobic layer and the porous diffusion layer, wherein each of the plurality of reservoirs is in fluidic communication with only one passage, thereby providing an exclusive pathway of fluidic communication between each of the plurality of reservoirs and the porous diffusion layer; and
      a controller operatively coupled to the driving electrodes and configured to provide a voltage gradient between at least two driving electrodes;
   coupling the porous diffusion layer to skin of a subject;
   moving a solution comprising an active molecule from one of the plurality of reservoirs to the porous diffusion layer; and
   allowing the active molecule to pass from the porous diffusion layer to the skin of the subject.

9. The method of claim 8, wherein the solution comprising an active molecule is held in the reservoir until the solution comprising an active molecule is required for delivery.

10. The method of claim 8, wherein a first reservoir contains a first solution comprising the active molecule at a first concentration and a second reservoir contains a second solution comprising the active molecule at a second concentration.

* * * * *